(12) United States Patent
Koehl et al.

(10) Patent No.: US 7,264,958 B1
(45) Date of Patent: Sep. 4, 2007

(54) METHOD FOR OBTAINING A PURIFIED VIRAL PREPARATION

(75) Inventors: Michel Koehl, Strasbourg (FR); David Gaillac, Strasbourg (FR)

(73) Assignee: Transgene, S.A., Strasbourg (FR)

( * ) Notice: Subject to any disclaimer, the term of this patent is extended or adjusted under 35 U.S.C. 154(b) by 0 days.

(21) Appl. No.: 09/914,036

(22) PCT Filed: Feb. 21, 2000

(86) PCT No.: PCT/FR00/00430

§ 371 (c)(1),
(2), (4) Date: Dec. 10, 2001

(87) PCT Pub. No.: WO00/50573

PCT Pub. Date: Aug. 31, 2000

(30) Foreign Application Priority Data

Feb. 22, 1999 (FR) .................................. 99 02167

(51) Int. Cl.
*C12N 7/02* (2006.01)
*A61K 39/235* (2006.01)

(52) U.S. Cl. .............................. 435/239; 435/4; 435/5; 435/7.1; 424/204.1; 424/233.1

(58) Field of Classification Search ............ 424/204.1, 424/233.1; 435/4, 5, 7.1, 173.9, 235.1, 239
See application file for complete search history.

(56) References Cited

U.S. PATENT DOCUMENTS 5,522,993 A 6/1996 Carlsson et al.
5,837,520 A * 11/1998 Shabram et al. ............ 435/239
6,027,888 A * 2/2000 Georgiou et al. ............... 435/6

FOREIGN PATENT DOCUMENTS

| DE | 41 28 953 | 3/1993 |
| EP | 0 328 256 | 8/1989 |
| WO | 89 08500 | 9/1989 |
| WO | 96 27677 | 9/1996 |
| WO | 97 06243 | 2/1997 |
| WO | 97 08298 | 3/1997 |
| WO | 98/00524 A1 | 1/1998 |
| WO | 98/22588 A3 | 5/1998 |
| WO | 98/26048 A1 | 6/1998 |
| WO | WO98/33572 A1 * | 8/1998 |
| WO | 99/40702 A1 | 8/1999 |
| WO | 99/54441 A1 | 10/1999 |

OTHER PUBLICATIONS

Hjorth, R. Expanded-bed adsorption in industrial bioprocessing: recent developments, Trends in Biotechnology, 1997, vol. 15:230-235.*
Bondoc et al. Size distribution analysis of recombinant adenovirus using disc centrifugation, Journal of Industrial Microbiology & Biotechnology (1998) 20:317-322.*
Haruna, I. et al; "Separation of Adenovirus by Chromatography on Deae-Cellulose", VIROLOGY, vol. 13, Jan. 1, 1961, pp. 264-267, XP 000601693.

* cited by examiner

*Primary Examiner*—Stacy B. Chen
(74) *Attorney, Agent, or Firm*—Buchanan, Ingersoll & Rooney, PC

(57) ABSTRACT

The invention concerns a method for purifying a crude viral preparation containing viral, in particular adenoviral, particles of interest. The invention is characterised in that it comprises a step of adsorption on a fluidised bed. The invention also concerns a protocol for producing viral particles for use in gene therapy comprising such a purifying process.

19 Claims, No Drawings

METHOD FOR OBTAINING A PURIFIED VIRAL PREPARATION

This application is a national stage filing under 35 U.S.C. § 371 of International Application No. PCT/FR00/00430 filed on Feb. 21, 2000. This application also claims benefit for foreign priority under 35 U.S.C. § 119 and/or 35 U.S.C. § 365 to Application No. 99/02167 filed in France on Feb. 22, 1999.

The present invention relates to a novel method for purifying a viral preparation. The present invention is most particularly valuable with a view of applications in the field of gene therapy, in particular applied to humans.

Gene therapy is defined as the transfer of genetic information which is of therapeutic interest or of interest in terms of immunization, into a host cell or organism with a view of obtaining, in this cell or this organism, a therapeutic or immunization effect. The first protocol applied to humans was initiated in the United States in September 1990 on a patient with an immunodeficiency linked to a mutation of the gene encoding adenine deaminase (ADA). In this particular context, it involved replacing the defective gene, the dysfunction of which was the cause of the genetic disease, with a functional gene. The relative success of this first experiment has encouraged the development of this technology, the application of which has since been extended to the treatment of other diseases, both genetic and acquired (cancers, infectious diseases such as, for example AIDS).

The implementation of gene therapy protocols is based mainly on the use of vectors which allow the transfer into, and optionally the expression of the genetic information of interest or gene in, a host cell or organism. Many vectors of viral and nonviral origin have been developed over the last few years and have been the subject of numerous publications available to those skilled in the art (for example, see Robbins et al., 1998, Tibtech, 16, 35-40 and Rolland, 1998, Therapeutic Drug Carrier Systems, 15, 143-198).

The value of viruses used as gene therapy vectors has already been referred to in the prior art. Among the most commonly used viruses, adenoviruses constitute vectors of choice since they can be used in the case of many cell types, regardless of whether they are dividing cells or quiescent cells, they are nonintegrating and they are relatively nonpathogenic. As described in patent applications No. WO 94/28152 or Wo 94/12649, they find many applications in the field of gene therapy. However, the properties of many other viruses have also been exploited for developing viral gene therapy vectors. By way of example, mention may be made of poxvirus vectors, and more particularly vectors derived from the vaccinia virus or from the Modified Virus Ankara (MVA; EP 324350), retroviral vectors (Naldini et al., 1996, Science 272, 263-267), etc.

Viruses, and in particular adenoviruses, currently used in gene therapy protocols are viruses in which the genome has been modified (by deletion, mutation, etc.) in such a way as to affect their replicative property with the aim of avoiding their propagation in the environment or the host organism, to reduce their immunogenic property and to allow the introduction of heterologous nucleic acid sequences of interest. More particularly, as described in particular in patent application WO 94/28152, the genome of these viruses can be specifically deleted of regions essential for the production of infectious viral particles. Similarly, patent applications EP 83286, EP 110385, U.S. Pat. No. 5,185,146 and WO 97/02355 describe the identification of naturally attenuated viral forms which can be used for the development of viral vectors. A virus in which at least one gene of interest is introduced into the genome is termed "recombinant virus" and, by extension, "recombinant vector"; more particularly, such recombinant viruses also comprise the elements suitable for the expression of these genes in host cells or organisms.

Viruses have the characteristic of multiplying in an essentially intracellular manner. Moreover, in the context of the implementation of gene therapy protocols, it is necessary to have viral particles, in particular infectious viral particles, which contain a vector of interest, in particular a recombinant vector of interest, associated with specific polypeptides, and which can be used as a product for gene therapy. There are known methods for producing viral particles which can be used in the context of gene therapy protocols, which comprise the following steps:

(i) producing a crude viral preparation,
(ii) purifying said crude viral preparation.

The crude viral preparation is obtained according to the following steps:

(a) infecting or transfecting a suitable cell line with at least one viral vector of interest, preferably a recombinant viral vector of interest;

(b) culturing said infected or transfected cell line under conditions which allow viral replication and the production of viral particles;

(c) collecting the cells;

(d) optional step for treating the cells, in particular according to a cell lysis protocol, so as to release the intracellular viral particles produced, in particular when the viral particles produced are not released into the medium during the culturing step;

(e) and, optionally, further treating the mixture obtained in step (c) or (d) with a DNase intended to limit the amount of cellular DNA and to decrease the viscosity of the mixture.

Besides the viral particles produced in the cells, the crude viral preparation also comprises all kinds of constituents, cellular debris, toxins, etc., which must be removed by carrying out one or more purification steps making it possible to obtain a preparation containing purified viral particles which can be used in gene therapy.

According to the known methods of the prior art, the purification of the crude viral preparation is carried out either by ultracentrifugation on a cesium chloride gradient (Huyghe, B et al., 1995, Human Gene Therapy, 6, 1403-1416) or by packed-bed adsorption (Huyghe, B et al., 1995, Human Gene Therapy, 6, 1403-1416).

Ultracentrifugation on cesium chloride gradient has many drawbacks. Specifically, cesium chloride is a toxic compound incompatible with therapeutic use in humans, which it is advisable to remove via a further purification step. Moreover, this technique of ultracentrifugation on cesium chloride gradient is especially suitable for treating small volumes of crude viral preparation. Specifically, ultracentrifugation devices allow the treatment of only about 600 ml of crude viral preparation. While such volumes are very suitable for productions intended for research studies, they do not make it possible to satisfactorily meet the constraints of industrial production. In addition, the ultracentrifugation technique cannot be automated. Finally, the amount of time required for carrying out this ultracentrifugation purification technique, approximately 40 hours, is also a very limiting element with industrial production in mind. Each of these drawbacks indicates that this technique for purifying a crude viral preparation is incompatible with the demands of yield and cost required by industrial companies.

The packed-bed adsorption purification method is based on the use of particles of adsorbent, sedimented or compacted together and placed in a chromatography column. According to this purification method, the crude viral preparation to be purified is loaded onto the column and the viral particles are purified using successive differential elutions. However, given the complex composition of the crude viral preparation, in particular comprising cellular debris, the chromatography column frequently clogs making the purification laborious and inefficient. In order to avoid this clogging, it is possible to carry out, before depositing the preparation on the chromatography column, a step for clarifying said crude viral preparation in order to remove the cellular debris. It is also proposed to carry out steps for concentrating, for adjusting the pH or for adjusting the conductivity of the crude viral preparation or passing it over the column. These additional and essential steps cause a decrease in the overall yield of the purification method, which does not allow production yields compatible with satisfactory industrial exploitation to be obtained.

In this context, it would be advantageous to have a novel method for preparing, from cell cultures, viral particles which are sufficiently pure for them to be used in gene therapy. More particularly, the methods described so far are not satisfactory in that they comprise steps which are limiting in terms of the volume of crude viral preparation to be purified (ultracentrifugation) and/or since they are too numerous, resulting in a decrease in the overall yield of about 5 to 20% which does not make it possible to satisfy exploitation on an industrial scale.

A novel method for purifying a crude viral preparation, which is entirely suitable for the industrial production of viral particles intended for gene therapy applications, has now been developed.

The present invention relates, firstly, to a method for purifying a crude viral preparation containing viral particles of interest, in particular adenoviral particles, characterized in that it comprises at least one fluidized-bed adsorption step.

The principle of fluidized-bed adsorption is briefly explained hereafter. More detailed explanations are available in "Expanded Bed Adsorption, Principles and Methods"—Pharmacia Biotech—Edition AA, and also in U.S. Pat. No. 5,522,993, the contents of which form part of the present description.

Unlike packed-bed adsorption, for which solid particles of adsorbent are sedimented or compacted together, fluidized-bed adsorption is based on the principle according to which solid particles of adsorbent included in said fluidized bed are maintained in suspension in a fluid (gaseous or liquid), thus generating free spaces between them. This suspension of the particles of adsorbent is obtained through the action of one or more forces (mechanical, electromagnetic, magnetic, gravitational, electrical, etc.). The suspension of the particles of adsorbent in a liquid or gaseous fluid can, for example, be obtained through the combination of a stream of said fluid flowing in the opposite direction to the gravitational field to which the adsorbent particles are naturally subjected. The direction and intensity of the two forces are easily chosen by those skilled in the art in order to maintain the particles of adsorbent in suspension. Similarly, it is possible to use the particles of adsorbent which have a particular composition which makes them sensitive to a magnetic and/or electrical force and thus makes it possible to obtain a suspension of particles of adsorbent as described above. Finally, it is also possible to have particles of adsorbent which, themselves, have a magnetic or electric charge sufficient to allow them to be suspended under suitable conditions. Those skilled in the art have the knowledge required for carrying out these variants of the invention.

The expansion, or suspending, of the particles of adsorbent generates the appearance of spaces between said particles, which allows cells, cellular debris or other unwanted particles, the removal of which from the crude viral preparation is desired, to pass.

According to the present invention, the particles of adsorbent used in the fluidized-bed adsorption step are in particular selected from particles consisting:

of organic and/or inorganic composite materials, such as for example silica, dextan-silica or cellulose-titanium dioxide (Gilcrist et al., 1994, Separations for Biotechnology, 3, pp. 184-190);

of polymers, such as for example agarose, polyacrylamide, polystyrene or derivatives thereof (for example poly(N-isopropylacrylamide), see CA2147115).

According to a particular embodiment, the particles of adsorbent also comprise a central core. Such a central core consists in particular of a core made of quartz or of inert metal (such as zirconium) (Hansson et al., 1994, Biotechnology, 12, 285-288; Hjorth et al., 1995, Bioseparation, 5, 217-223) or of a core, the composition of which allows said particles of adsorbent incorporating it to be maintained in suspension in the fluid by applying a magnetic, electrical or electromagnetic field (see, for example "Continuous cell suspension processing using magnetically stabilized fluidized beds", Biotechnology and Bioengineering, Vol. 37, pp. 110-120 (1991) by B. E. Terranova and M. A. Burns).

According to a preferred case of the invention, the particles of adsorbent bear, directly or indirectly, at least one ligand capable of binding specifically and reversibly to an antiligand. In accordance with the present invention, a said antiligand consists of all or part of a viral particle of interest, the purification of which from a crude viral preparation is desired.

The term "ligand" is intended to denote:

all or part of the polypeptide capable of binding specifically and reversibly to all or part of a protein of said viral particle of interest, in particular a capsid or envelope protein, a protein located at the surface of the adenoviral particle, such as the hexon, the pentons (Hong et al., 1995, EMBO J., 14, 4712-4727) or the fiber (Henry et al., 1994, J. Virol, 68, 5239-5246), etc. In particular, it may be all or part of an antibody, of a specific membrane receptor, of a recombinant peptide or of protein A;

all or part of a molecule other than a polypeptide capable of reversibly binding said viral particle of interest or a constituent thereof (one of the proteins mentioned above). By way of examples, mention may be made of heparins and the affinity ligands used in IMAC (Immobilized Metal Affinity Chromatography);

a positively charged group, in particular as basic group, bearing, for example, a substituted amine, in particular an amine substituted with alcohol groups; preferably, a basic charged group selected from the dimethylaminoethyl (DMAE) group, the diethylaminoethyl (DEAE) group, the trimethylaminoethyl (TMAE) group, the group $-R-CH(OH)-CH_2-N^+-(CH_3)_3$ (also termed Q group; see Streamline® resins—Pharmacia), the guanidinium group or the imine groups, such as polyethyleneimine (PEI), will be chosen;

a negatively charged group, such as for example a sulfate group of formula $R-SO_4^-$ with, for example, R=alkyl groups (for example methyl sulfate) or a carboxylate group of formula R—COO⁻ with, for example, R=alkyl groups (for example methyl carboxylate), or alternatively a phosphate group of formula R—PO₄⁻ with, for example, R=alkyl groups.

Such positively or negatively charged ligands are capable of binding specifically to oppositely charged antiligands.

In the context of the present invention, the preferred particles of adsorbent consist of an agarose matrix and comprise a central core made of quartz and dextran chains covalently coupled to the agarose matrix, on which are attached the positively charged groups. Entirely preferably, the particles of adsorbent are the Streamline® resins of the XL type sold by Pharmacia and, most particularly, the Streamline® Q XL resin consisting of an agarose matrix (6%) and comprising a central core made of quartz and dextran chains covalently coupled to the agarose matrix, and which are attached the Q groups.

The invention also relates to the case in which said ligand is indirectly attached to the particle of adsorbent. In this case, said ligand is attached via a chemical arm which does not interfere with the reactivity of said ligand with regard to the antiligand. Such arms and also the use thereof are widely described in the literature relating to chemical syntheses.

It is also possible to choose the pH at which the method of the invention will be carried out, so as to optimize the specific ligand/antiligand binding, in particular when particles of adsorbent bearing a charged ligand are used. Thus, when the use of particles of adsorbent carrying basic groups, in particular for purifying adenoviral particles in which the surface proteins have mostly isoelectric points (pI) of between 5.3 and 6.0 is chosen, the pH will be between approximately 6 and approximately 10, advantageously between approximately 7.5 and approximately 9.5 and will preferably be approximately 8.5, so that most of the viral proteins are negatively charged and interact with the basic groups of the particles of adsorbent. Conversely, when the method according to the invention uses particles of adsorbent carrying negatively charged groups, the pH chosen will be between approximately 3.0 and approximately 5.0. Moreover, it is also possible to work at pHs lower than the pI of the viral proteins, in particular when particles of adsorbent carrying a negatively charged ligand are used. In this particular case, it is necessary to use a buffer with high conductivity in order to stabilize the viral particles. Those skilled in the art are capable of adjusting the pH using buffered solutions or by adding bases or acids in order to increase or decrease, respectively, the pH as required.

In order to carry out the method of the invention, the ligand must be capable of binding reversibly to the antiligand of interest. Those skilled in the art are capable of establishing the optimum conditions as a function of the ligand, of the antiligand and of the particles of adsorbent used. By way of indication, a buffer equilibrated at a final NaCl concentration of 400 mM is particularly suitable for carrying a method according to the invention using the Streamline® Q XL resin for purifying recombinant adenoviruses. The ligand/antiligand dissociation may be produced by any suitable means, and in particular by modifying the salinity or the pH of the reaction medium. Preferably, the dissociation is produced by increasing the salinity.

In addition, according to the invention, it is possible to monitor the purification method, in particular continuously, on the samples harvested and treated according to the method of the invention, by any means known to those skilled in the art. It is in particular possible to perform spectrophotometric measurements of the adsorbents at 260 nm and 280 nm, and to calculate the OD260/OD280 ratio in each sample, in the knowledge that all purified viral preparations have a characteristic OD260/OD280 ratio. By way of indication, the OD260/OD280 ratio of a purified adenoviral preparation is approximately 1.25 (1.22 to 1.28). It is also possible to monitor the purification method using conventional detection techniques, such as for example electrophoresis, PCR and immunofluorescence techniques and techniques for determining the viral titer.

The temperature at which the method according to the invention is carried out is preferably between −5 and +50° C. However, in order to preserve the infectious properties of the viral particles, the purification of which is desired, a temperature of between approximately +4° C. and +37° C., and more particular between approximately +15° C. and +25° C., will be preferred.

According to a preferred embodiment, the method according to the invention is carried out under conductivity conditions of between approximately 25 and approximately 70 mS/cm, advantageously between approximately 30 and approximately 40 mS/cm, and preferably between approximately 30 and approximately 35 mS/cm. However, it is within the scope of those skilled in the art to vary the conductivity according to the nature of the contaminants and the composition of the medium of the culture in the viral particles. Advantageously, the viral particles of interest and the particles of adsorbent are equilibrated with the same conductivity conditions.

When the fluidized bed is formed, i.e. the particles of adsorbent are in suspension, it is possible that these particles perform a permanent circular movement which is known as "recirculated rolling". This phenomenon decreases the absorption capacity of the particles and should, consequently, be limited as much as possible. A possible solution consists in using particles of adsorbent of heterogeneous sizes. Specifically, the heterogeneous distribution of the sizes enables the particles of adsorbent with the smallest volume to be located in the upper part of the device, for example a column, which contains them. Conversely, the largest particles are located in the lower part of said device, which makes it possible to considerably decrease the mobility of the particles.

Consequently, the particles of adsorbent according to the invention will preferably be chosen such that they have heterogeneous sizes.

Another solution for avoiding the formation of recirculation rolling consists in compartmentalizing the device in order to limit the possibilities of movement of the particles of adsorbent (A. Buijs and J. A. Wesselingh, 1980, Journal of Chromatography, Vol. 201, pp. 319-327).

As mentioned above, for carrying out the method according to the invention, the particles of adsorbent are maintained in suspension in a device. Advantageously, said device is cylindrical in shape and, preferably, it is a chromatography column. In a preferred embodiment of the method according to the invention, a chromatography column as described in U.S. Pat. No. 5,522,993 will be chosen. This column has, at each of its ends, at least one inlet or outlet through which the effluent and eluant solutions entering and leaving the column circulate. According to this particular case, the particles of adsorbent are, initially, subjected to an expansion phase, in particular by applying, in the chromatography column, an ascending flow of buffer obtained by introducing the buffer through the inlet located at the lower end of the column and evacuating it through the outlet located at the upper end. This expansion phase is maintained until a "fluidized bed" is obtained, i.e. an equilibrium is obtained between the force of earth's gravity which attracts the particles of adsorbent toward the lower end of the column, and the entrainment forces of the ascending flow of the buffer, which are directed toward the upper end of the column.

In accordance with the present invention, the crude viral preparation is subjected to a purification method comprising one step at least of fluidized-bed adsorption. More particularly when the device is a column, after obtaining the "fluidized-bed", the crude viral preparation to be purified is loaded onto the column. In the preferred case of the invention in which said column is as described in U.S. Pat. No. 5,522,993, the crude viral preparation is introduced into the lower part of this column. Next, the crude viral preparation is washed by passing buffer through. In the preferred case, the buffer is passed through in an ascending flow. After the washing phase, the flow of buffer is stopped in order to allow the particles of adsorbent to sediment. According to a preferred case, this sedimentation phase is aided by a descending flow of buffer. An elution step is then conducted by applying a flow of buffer, in particular a descending flow, under conditions of concentration, of pH and/or of conductivity which those skilled in the art are capable of adjusting in order to allow the release of the viral particles adsorbed onto the adsorbent particles. Similarly, it is within the scope of those skilled in the art to adjust the chromatography conditions as a function of various parameters, in particular of the column volume, of the particles of adsorbent chosen, of the height of the particles of adsorbent in said column (generally from 10 to 50 cm, advantageously from 10 to 40 cm, and preferably around 30 cm), of the flow rate (from 50 to 600 cm/h, advantageously from 100 to 400 cm/h, and preferably around 300 cm/h, particularly for a column of Streamline® Q XL resin with a height of approximately 30 cm), of the viral concentration, of the load and/or of the nature of the contaminants. The viral preparation may, for example, be eluted by modifying the salinity or the pH of the eluant.

The method according to the invention may also comprise additional steps prior to or subsequent to the fluidized-bed chromatography. According to an optional embodiment, the eluted viral fractions obtained after the fluidized-bed chromatography step can be pooled and optionally concentrated according to the techniques of the art. Mention may be made in particular of tangential ultrafiltration and diafiltration. The BioMax PES (Millipore reference PXB300C50) and PLCMK (Millipore reference PXC300C50) cassettes are most particularly suitable. This concentrating step is most particularly indicated when perfecting the purity of the viral particle preparation with an additional step of chromatography other than fluidized-bed chromatography is envisioned. This concentrating step makes it possible to place the viral particles in a medium suitable for carrying out this second chromatography.

According to a particular embodiment, the method for purifying the crude viral preparation according to the invention may also comprise a packed-bed chromatography step and, preferably, a gel filtration chromatography step. The two steps (fluidized-bed adsorption step and packed-bed chromatography) can be carried out in any order; however, preferably, the fluidized-bed adsorption step will be carried out first, followed by the packed-bed chromatography, in particular a gel filtration chromatography.

According to the gel filtration chromatography step, the sample is treated on a solid support comprising beads with a diameter of between 3 and 160 µm, advantageously between 5 and 105 µm, and preferably between 10 and 80 µm. Preferably, this support has a porosity close to the size of the virus so that the latter does not penetrate into the beads. On the other hand, the molecules which are smaller in size penetrate into the beads and the migration thereof is slowed. Various types of support may be used, such as matrices based on agarose (Sepharose™), on dextran (Sephadex™ gel), on acrylamide (Sephacryl™ and Trisacryl gels), on silica (TSK and SW gels), on ethylene glycol/methacrylate copolymers (Biosec BioSEC, Toyopearl® HW, TSK and PW gels) and on mixtures, in particular mixtures of agarose and dextran (Superdex™ gel). The supports mentioned are preferably used without the functionalization group. The gel filtration chromatography supports which are particularly suitable for carrying out the preparation method according to the invention are as follows:

allyl dextran/methylene bisacrylamide matrices (Sephacryl™ S300 HR with a bead diameter of between 25 and 75 µm, Sephacryl™ S400 HR with a bead diameter of between 25 and 75 µm, Sephacryl™ S500 HR with a bead diameter of between 25 and 75 µm and Sephacryl™ S1000 SF with a bead diameter of between 40 and 105 µm;l Pharmacia),
  ethylene glycol/methacrylate matrices (Toyopearl® HW 55, Toyopearl® HW 65 and Toyopearl® HW 75, with a bead diameter ranging from 20 to 60 µm; Tosohaas),
  N-acrylaminohydroxypropanediol matrices (Trisacryl with a bead diameter of between 80 and 160 µm; Biosepra), or
  agarose matrix (Macro-Prep SE with a bead diameter of between 20 and 80 µm; Bio-Rad).

By way of indication, it will be noted that a support of the Toyopearl® HW65F or S (porosity 1000 Å) or Sephacryl™ S400 HR type is preferred. Such a column is equilibrated in a buffer exhibiting saline conditions and a pH limiting the hydrophobic interactions between the support and the viral particles. Advantageously, use will be made of a 25 mM Tris-HCl buffer containing 2 mM $MgCl_2$, 2% sucrose, at pH 8.5, or a 10 mM Tris-HCl buffer containing 10 mM sodium aspartate, 54 mg/l of Tween® 80 and 2% sucrose, at pH 8.5. The viral particles of interest are eluted without being retained and leave the column before the contaminants of lower molecular weight or smaller size. According to an optional embodiment, the viral fractions obtained after the purification step may be pulled and optionally concentrated according to conventional techniques. Mention may be made of tangential ultrafiltration and diafiltration. The BioMax™ PES (Millipore reference PXB300C50) and PLCMK (Millipore reference PXC300C52) cassettes are most particularly suitable.

The invention also relates to a protocol for producing viral particles which can be used for gene therapy, comprising the following steps (i) and (ii):
  (i) production of a crude viral preparation, comprising the steps:
    (a) infecting or transfecting a suitable cell line with at least one viral vector of interest, preferably a recombinant viral vector of interest;
    (b) culturing said infected or transfected cell line under conditions which allow viral replication and the production of viral particles;
    (c) collecting the cells and/or the supernatant,
  (ii) purification of said crude viral preparation according to a method characterized in that it comprises at least one fluidized-bed adsorption step as described above.

According to a preferred particular case, after step (c) for collecting the cells, a cell rupture or lysis step is carried out, generally after resuspending the cellular biomass collected, in order to allow the release of the viral particles produced in an intracellular manner. All conventional means may be used, in particular chemical and/or mechanical means. Freezing/thawing cycles which weaken the cell membranes, enzymatic lysis (the use of enzymes which degrade the cell membranes) or chemical lysis (the use of detergent, pH shock, etc.) may, for example, be carried out. The mechanical means may be the result of ultrasound (sonication), of attrition (DynoMill or BeadMill glass beads), of pressure and shear forces (French Press high pressure homogenizer), of microfluids (Microfludics, Newton, Mass.) or of the mechanical action of two cylinders generating hydraulic and mechanical shear forces (Silverson homogenizer).

However, although it is not excluded, this cell rupture/lysis step is not obligatory in the particular case in which the viral particles are released into the culture medium. In this case, step (ii) may be directly applied to the sample containing both the cells and the medium, or exclusively to the culture supernatant which contains the viral particles to be purified.

The protocol according to the invention may also comprise a clarification step, the aim of which is to remove insoluble matter (cellular debris, flocculates of macromolecules, etc.) possibly produced during the cell rupture or lysis step. It may be carried out using any conventional technique of filtration (depth filtration, tangential microfiltration, etc.) or centrifugation (continuous centrifugation, etc.) Many filters may be used on the condition that they have a porosity which enables the viral particles to pass through and the insoluble matter to be retained. It is indicted that adenoviral particles are approximately 0.07 to 0.1 µm in size, which necessitates the use of filters with a high porosity. Furthermore, the filters may be made of synthetic material (nylon), organic material (cellulose) or nonorganic material (zirconium). According to an advantageous embodiment, successive filtrations are carried out over filters with decreasing porosity, for example initially over a filter with a porosity of 8 µm (Sartorius® 5591301P5-00) then over a filter with a porosity of 5 µm (Sartorius 5591342P5-00), then over a filter with a porosity of 3-0.8 µm (Sartorious, Sartoclean® capsule 5621304E9-00-A) and then, optionally, over a filter with a porosity of between 0.8 and 0.65 µm (Sartorious, Sartoclean® CA capsule 5621305G9-00-A). According to another variant, the filtration may be carried out by tangential microfiltration over flat membranes or hollow fibers with a porosity greater than the size of the adenovirus. In this regard, Durapore® (Millipore) and Omega™ (Pall) membranes may be used.

In addition, the protocol for producing viral particles which can be used in the context of gene therapy protocols, according to the invention, may comprise at least one step for degrading the nucleic acids present in considerable amounts after the rupturing of the cells. To this effect, nonspecific restriction enzymes of the endonuclease or exonuclease type may be used. According to a preferred embodiment, the enzyme chosen is benzonase, optionally in the presence of β-cyclodextrin which facilitates the precipitation of lipids (recommended final concentrations of 5 to 50 U/ml of benzonase and of 0.1 to 10%, and in particular 1.5%, of β-cyclodextrin).

The protocol of the invention may also comprise an optional step for inactivating enveloped viruses. This step makes it possible, in particular in the case of adenoviral preparations, to improve the safety of the final product and to increase the quality of the purified adenoviral preparation. An example of an enveloped virus inactivation step is given in French patent application No. 98/16147. It is possible to carry out the inactivation step and the nucleic acid degradation step concomitantly.

The protocol for producing viral particles according to the invention may also comprise a sterilizing filtration step, said sterilizing filtration step preferably being carried out after step (c) or (ii) of said preparation method. Use would advantageously be made of 0.22 µm filters. Mention may be made, for example, of filtration units of the Minisart® (Sartorius, reference SM16534), Sartolab® P20 (Sartorius, reference 18053D), Millex® GF (Millipore, reference SLGS025BS), Millex® GV (Millipore, reference SLGV025BS), Millex® GP (Millipore, reference SLGPR25LS) or alternatively Spirale Cap (Super CQS 92 HS or HP version; Gelman Sciences), CritiCap® 50 (12995, Gelman Sciences) or Millipak® (Millipore, reference MPGL04SK2 or MPGL02SH2) type.

The method for purifying a crude viral preparation and the protocol for producing viral particles, according to the invention, relate in particular to viral preparations comprising viral particles of interest for applications in gene therapy, and in particular for preparing immunization preparations, such as for example adenoviral, poxyiral, iridoviral, papovaviral, rotaviral, parvoviral, hepadnaviral, herpetic, reoviral, coronaviral, flaviviral, togaviral, mononegaviral, arenaviral, bunyaviral, orthomyxoviral, calciviral or picornaviral particles. Preferably, these viral particles contain a recombinant virus. According to the present invention, the crude viral preparation, the purification of which is intended, may contain one or more viral particles of different viral origins.

The implementation of the methods and protocols of the invention is most particularly suitable for obtaining purified adenoviral particles comprising replication-defective recombinant adenoviruses. The term "recombinant" refers to the presence of at least one gene of interest placed under the control of the elements suitable for its expression in a host cell. The term "replication-defective" means that the available genetic information does not permit the autonomous replication of the virus under consideration in a host cell. In this case, the production of viral particles requires the infection or transfection, by any suitable means, of suitable cells, termed complementation cells, with the deficient, generally recombinant virus. These complementation cells provide, in trans, the information required for the replication and assembly of the deficient viruses in the form of viral particles. Such lines, and also the use thereof, are widely described in the literature (see, for example, application WO 94/28152 or WO 97/00326; the 293 line, Graham et al., 1977, J. Gen. Virol. 36, 59-72; Lusky et al., 1998, J. Virol 72, 2022-2032). With regard to other viruses, they require cell culture conditions which are more specific but completely mastered (see, for example, W. MVA, retroviruses, etc.). The infected or transfected complementation cells are cultured under widely described conditions, for a period of time sufficient to allow the viruses to replicate and the viral particles to assemble.

Other characteristics and advantages of the present invention will become apparent upon reading the examples hereinafter. However, the invention cannot be limited to the content of said examples.

EXAMPLES

The recombinant adenoviruses used in the examples which follow were constructed using the homologous recombination technique described in Chartier et al. (1996, J. Virol. 70, 4805-4810). The constructs used were prepared according to the general techniques of genetic engineering and of molecular cloning, detailed in Maniatis et al., (1989, Laboratory Manual, Cold Spring Harbor, Laboratory Press, Cold Spring Harbor, N.Y. or a more recent edition) or according to the manufacturer's recommendations when a commercial kit is used. The cloning steps use the *E. coli* strain 5K (hsdR, mcrA), DH5a [(recA1, endA1, hodR17 (r-m-), supE44, thi-1, gryA (nair)] or NM522 (supE, thi, D(lac-proAB), Dhsd5, (r-m-), (F' proAB, lacI$^q$, ZDM15) and those of homologous recombination use the *E. coli* strain BJ 5183 (Hanahan, 1983, J. Mol. Biol. 166, 557-580). As regards repairing the restriction sites, the technique used consists in filling the overhanging 5' ends using the large fragment of *E. coli* DNA polymerase I (Klenow, Boehringer Mannheim). The DNA fragments are purified using the GeneCleanII® DNA purification kit (Bio101Inc.). Moreover, the fragments of adenoviral genome used in the various constructs are precisely indicated according to their position in the nucleotide sequence of the Ad5 genome, as disclosed in the Genebank data bank under the reference M73260.

With regard to cell biology, the cells are transfected or transduced and cultured according to the standard techniques well known to those skilled in the art. Use is made of the 293 (ATCC CRL-1573), A549 E1+ (WO 94/28152) and 293-E40RF6+7 (Lusky et al., 1998, J. Virol. 72, 2022-2032) cell lines. It is understood that other cell lines may be used. The cells are maintained in culture at 37° C. in a humid atmosphere enriched with 5% $CO_2$, in DMEM (Dulbecco's Modified Eagle Medium, Gibco BRL) medium supplemented with 1 mM of glutamine, 1% of amino acids (Gibco BRL), 40 mg/l of gentamycin and 10% of fetal calf serum (SVF, Gibco BRL). The cells are transfected according to the techniques of the art (calcium phosphate precipitation, etc.).

The following examples were carried out using recombinant adenoviruses expressing a marker gene or a therapeutic gene. They are derived from the Ad5 serotype and have the following structure:

AdTG6297 is an adenoviral vector defective for the E1 (deletion of nt 459 to 3328) and E3 (deletion of the XbaI fragment extending from nt 28592 to 30470) functions, into the genome of which is inserted, as a replacement for the E1 region, an expression cassette for the marker gene encoding the GFP protein (for green fluorescent protein). The latter reacts to light excitation (485 nm) by emitting a fluorescent light, the intensity of which is measured a filter (535 nm). More precisely, the cassette is composed of the CMV promoter followed by a chimeric intron, of the sequence encoding the GFP protein and of the polyA of the SV40 virus. The intronic sequences are isolated from the pCI plasmid (Promega Corp, pCI mammalian expression vector E1731) and comprise the splice donor site of intron 1 of the human b-globin gene and also the branching point and the splicer acceptor site of the gene of a mouse immunoglobin. The viral particles are produced by transfecting the AdTG6297 vector into an E1-complementation line (293 or A549 E1+) and amplified by successive passages on a permissive line (E1-completing line).

The AdTG5643 vector is a vector deleted of the E1 (nt 459 to 3328), E3 (nt 28592 to 30470) and E4 (nt 32994 to 34998) regions and expressing the human CFTR therapeutic gene. The expression cassette consists of the CMV early promoter, of the CFTR cDNA and of the poly A of the rabbit b-globin gene, and is inserted in place of the deleted E1 sequences. The viral particles are produced by transfecting the AdTG5643 vector into an E1 and E4-complementation line (293-E40RF6+7) and a viral stock is made by successive passages on a permissive line (E1 and E4-complementing line).

The AdTG13383 vector is a vector deleted of the E1 (nt 459 to 3511) and E3 (nt 28539 to 30470) regions and expressing the human IL2 therapeutic gene. The expression cassette consists of the CMV early promoter, of the synthetic intron isolated from pCI (described above), of the cDNA encoding human IL-2 and of the SV40 poly A, and is inserted in place of the deleted E1 sequences. The viral particles are produced by transfecting the vector pTG13383 into an E1-complementation line. A viral stock is made by successive passages on a permissive line (E1-complementing line).

Example 1

Preparation of Virus from the Complementation Cells

The A549-E1+ cells are cultured in the culture dishes until a concentration of $1 \times 10^6$ cells/ml is reached and are then infected with a prestock of AdTG6297 at an MOI of approximately 3. The infected cells are harvested 72 h post-infection and centrifuged at low speed. The pellet is taken up in approximately 600 ml of culture medium without serum. The preparation thus obtained corresponds to a volume of approximately 20 l of culture.

The intracellular viral particles are released after rupturing of the cells subjected, from 7 to 10 min, to the mechanical action of a Silverson homogenizer (L4R-Silverson) set at a rotation rate of 4200 rpm. At this stage, the preparation is very viscous due to the release of the genomic DNA following cell rupture. A volume of a buffer which allows optimum-action of benzonase and consists of 100 mM Tris, 4 mM $MgCl_2$ and 4% sucrose, pH 8.5, to which has been added the solubilization agent Tween® 80 (Merck reference 8-22187-1000) at a concentration of 2%, is added to the viral preparation. The mixture is stirred at room temperature before adding benzonase in a proportion of 50 U/m (Merck reference 101697) and the reaction is allowed to continue for 1 to 2 h at room temperature and with stirring.

Example 2

Preparation of Virus from the Cell Culture

Example 1 is reproduced with the difference that the cells and the culture supernatant (volume of approximately 20 l) are harvested 72 h post-infection and the mixture is directly subjected to the rupture step so as to obtain the crude viral preparation to be purified.

Example 3

Purification of the Crude Viral Preparation Using a Fluidized-Bed Chromatography Step The aim of Example 3 is to illustrate an embodiment of the method according to the invention for obtaining purified viral particles.

Initially, any one of the crude viral preparations obtained in Examples 1 and 2 is subjected to a step for inactivating enveloped viruses. This inactivation step is carried out through the action of TNBP/Tween® 80(tributylphosphate ref.: 24 0494 Aldrich) at a final concentration of 0.3% and 1%, respectively. To do this, the crude viral preparation obtained in Example 1 or 2 is diluted volume-for-volume in a 50 mM Tris buffer solution containing 2 mM $MgCl_2$, 2% sucrose, 450 mM NaCl and 0.6% TNBP (Aldrich 24-049-40), pH 8.5 It is also possible to add to the viral preparation 1/10 of a volume of a more concentrated 50 mM Tris buffer solution containing 1 mM $MgCl_2$, 2% sucrose, 2 M NaCl and 3% TNBP (Aldrich 24-049-40), pH 8.5. It should be noted that the saline conditions use (400 mM NaCl final) correspond to the equilibration conditions of the chromatography. The action of the TNBP/Tween® 80 continues with stirring (500 rpm) for 3 hours at room temperature or for 4 hours at 4° C.

The inactivated crude viral preparation is then subjected to fluidized-bed ion-exchange chromatography. To do this, the viral preparation is loaded onto a column containing a resin of the Streamline® QXL type (ref. Pharmacia 17-5075-01) pre-equilibrated using a 50 mM Tris buffer containing 2 mM $MgCl_2$, 2% sucrose, 400,mM NaCl, pH 8.5. The buffer is introduced at the bottom of the chromatography column and is made to leave at the top of the column, so as to create an ascending flow of buffer in the column. A flow rate of 100 to 300 cm/h, and preferably 150 cm/h, is used to equilibrate and load the column with the crude viral preparation to be purified. The viral preparation applied onto the column is then rinsed with various passages of buffer solution in the ascending and descending direction. The aim of this operation is to remove a first range of contaminants which have adsorbed via non-ion-specific interactions or which are mechanically trapped. The various cell constituents adsorbed onto the chromatography support via ion-specific interactions are then gradually eluted by applying an equilibrating buffer containing increasing concentrations of salt (425 mM, 450 mM, 500 mM NaCl). A flow rate of 50 to 150 cm/hour, and preferably of 100 cm/hour, is applied once the flow of buffer is descending. The eluate is recovered in fractions. Each fraction is analyzed by measuring the adsorbance at 260 and 280 mm. Generally, the proteins which are detected only at 280 nm are eluted by the buffer containing a NaCl concentration of 425 mM. A second elution peak is detected at 280 and 260 nm. It contains the adenoviral particles of interest and is eluted by the buffer having a saline concentration of 450 mM. The fractions corresponding to this second elution peak are pulled and optionally subjected to gel filtration chromatography.

The fluidized-bed chromatography column can be regenerated, washed and treated with the series of steps shown in Table 1:

TABLE 1

| Solution | Concentration | Column volume (Vc) | Flow rate (cm/h) | Direction |
|---|---|---|---|---|
| NaCl | 1.5 M | 4 | 100 | Descending |
| HCl | 0.05 N | 9 | 30 | Ascending |
| $H_2O$ | — | 6 | 100 | Ascending |
| NaOH | 1 N | 12 | 30 | Ascending |
| NaCl | 3 M | 9 | 30 | Ascending |
| Tris-Hcl | 10 mM | 9 | 30 | Ascending |
| EDTA pH 8.0 | 1 mM | | | |

The gel can then be stored in 0.01 M NaOH for several weeks.

The yield from a method for obtaining viral particles can be calculated in the following way:

| Steps | Total IU × $10^{13}$ | % yield (overall) | % yield (step) |
|---|---|---|---|
| Start | 2.69 | 100 | — |
| Benzonase | 2.74 | 102 | 102 |
| Inactivation | 2.58 | 96 | 94 |
| SQXL | 2.11 | 78 | 82 |

IU represents the number of infectious units

The method of the invention makes it possible to purify a volume of about 20 liters of crude viral preparation while at the same time obtaining an overall yield of approximately 80% after the fluidized-bed chromatography step, whereas the methods of the prior art make it possible, at best, to obtain yields of about 60% after the packed-bed chromatography step.

Example 4

Preparation of a Clinical Batch of Infectious Adenoviral Particles for Anticancer Purposes (Transfer of the IL-2 Gene).

The E1-complementation cells are cultured in a bioreactor in ExCell 525 medium (JRH Biosciences) until a concentration of $1 \times 10^6$ cells/ml is obtained and are then infected with an aliquot of an AdTG13383 prestock, at an MOI of approximately 10. The infected cells and the culture supernatant (volume of approximately 20 l) are harvested 72 h post-infection. The intracellular viral particles are released after rupturing of the cells subjected, for 7 to 10 min, to the mechanical action of a Silverson homogenizer (275 UHLS) set at a rotation rate of 50 Hz (rate of 8.1).

The crude viral preparation thus obtained is subjected to a clarification step in order to remove the insoluble matter (cellular debris, flocculates of macromolecules, etc.). Successive filtrations are carried out over filters of decreasing porosity, first of all over a filter with a porosity of 8 μm (Sartopure® 300PP2 5592501) then over a filter with a porosity of 5 μm (Sartopure® 300 PP3 5592542) and, finally over a filter with a porosity of between 3 and 0.8 μm (Sartorius, Sartoclean CA capsule 5621304E9-00-A).

The clarified viral preparation is subjected to a step for degrading the DNA (Benzonase action) and, concomitantly, to a step for inactivating enveloped viruses (action of the 0.3% TNBP/1% Tween® 80 mixture). To do this, one volume of a 100 mM Tris buffer containing 4 mM $MgCl_2$ and 4% sucrose, pH 8.5, comprising Tween® 80 (Merck reference 8-22187-1000) at a concentration of 2%, is added to the clarified viral preparation. The mixture is stirred at room temperature before adding benzonase in a proportion of 10 U/ml (Merck reference 101697) and TNBP (Aldrich 24-049-40) at a final concentration of 0.3%. The reaction is allowed to continue for 2 h at room temperature with stirring (500 rpm).

The viral preparation thus obtained is diluted in a volume of 50 mM Tris, 2 mM $MgCl_2$, 2% sucrose and 2M NaCl, so as to obtain a conductivity of 35 mS/cm which is optimal for carrying out fluidized-bed ion-exchange chromatography.

The conductivity-adjusted viral preparation is loaded onto a column containing a resin of the Streamline® Q XL type (ref. Pharmacia 17-5075-01) pre-equilibrated using a 50 mM Tris buffer containing 2 mM MgCl$_2$, 2% sucrose and 360 mM NaCl, pH 8.5. The buffer is introduced at the bottom of the chromatography column and made to leave at the top of the column, so as to create an ascending flow of buffer in the column. A flow rate of 300 cm/h is applied during the equilibrating and the loading of the column with the viral preparation. Once the loading has taken place, the column is then rinsed with various passages of buffer solution in the ascending and descending direction, with the aim of removing the contaminants which have been adsorbed by non-ion-specific interactions or which are mechanically blocked. The various cell constituents absorbed onto the chromatography support via ion-specific interactions are then gradually eluted by applying an equilibrating buffer containing increasing concentrations of salt (650 mM, 2 M NaCl). A flow rate of 150 cm/hour is applied once the flow of buffer is descending. The eluted fractions are analyzed by measuring the adsorbance at 260 and 280 nm. The viral particles adsorbed at the two wavelengths with an OD 260/OD 280 ratio of approximately 1.25 (1.22 to 1.28) and, generally, the elution peak is located in a saline concentration region of 650 mM.

The fluidized-bed chromatography column can be regenerated and washed according to the protocol indicated above.

The fractions obtained after the fluidized-bed chromatography and containing the adenoviral particles are concentrated by diafiltration on Labscale™ (Millipore) using the BioMax™ PES cassettes (Millipore reference PXB01MC50) or cellulose membranes with a cutoff threshold of 300 kDa and 1000 kDa.

The concentrated viral preparation is then subjected to gel filtration chromatography. To do this, the viral preparation is loaded onto a column containing a resin of the Toyopearl® HW65F type (ref. Tosohaas 07 465) pre-equilibrated using a 10 mM Tris buffer containing 54 mg/l Tween® 80, 2% sucrose and 10 mM sodium aspartate, pH 8.5. The buffer is introduced through the top of the chromatography column and is made to leave through the bottom. A flow rate of 30 cm/h is used to equilibrate and load the column with the concentrated viral preparation. The viral preparation applied on to the column (approximately 20% of the column volume) is then rinsed with the buffer which enables the column to be equilibrated (10 mM Tris, 54 mg/l Tween® 80, 2% sucrose, 10 mM sodium aspartate, pH 8.5) in the descending direction. The aim of this operation is to remove the low molecular weight contaminants which have been slowed down by passing through the pores of the gel, unlike the virus which is excluded from the gel beads. The various cell constituents which have been slowed down on the chromatography support are then gradually eluted, still with the same buffer. The eluate is recovered in fractions. Each fraction is analyzed by measuring the adsorbance at 260 and 280 nm. Generally, the first peak detected at 280 and 260 nm contains the adenoviral particles of interest, whereas the protein contaminants detected only at 280 nm are eluted in the second position. The fractions corresponding to the first peak are pulled, optionally concentrated by diafiltration, placed in a buffer with a suitable formulation (for example in saline or isotonic solution) and then filtered over 0.22 µm Sartolab P20 (Sartorius, reference 18053D) and stored until use.

The yield from a method for obtaining viral particles can be calculated in the following way:

| Steps | % IU yield (overall) | % IU yield (step) | % TP yield (overall) | % TP yield (step) |
|---|---|---|---|---|
| Start | 100 | — | 100 | — |
| Clarification | 96 | 96 | 78 | 78 |
| Dnase/Inactivation | 130 | 135 | 112 | 144 |
| SQXL | 107 | 82 | 88 | 78 |
| Concentration/diafiltration | 107 | 100 | 86 | 98 |
| Gel filtration | 86 | 80 | 77 | 90 |

IU represents the number of infectious units, determined by quantitatively measuring the immunofluorescence with an anti-DBP antibody as described in Lusky et al. (1998, J. Virol 72, 2022-2032).

TP represents a total number of viral particles, determined by measuring the adsorbents at 260 and 280 nm.

The method of the invention makes it possible to purify a volume of about 20 liters of crude viral preparation while at the same time obtaining an overall yield of approximately 90% after the fluidized-bed chromatography step, whereas the methods of the prior art make it possible, at best, to obtain yields of about 60% after the packed-bed chromatography step. And an overall yield of 77 to 86% after the gel filtration step.

The invention claimed is:

1. A method for purifying infectious adenoviral particles from a crude viral preparation containing said adenoviral particles, comprising:
    i) a fluidized bed chromatography step comprising at least the steps of:
        a. contacting said crude viral preparation with particles of adsorbent in fluidized bed under suitable conditions to allow adsorption of said adenoviral particles onto said particles of adsorbent,
        b. eluting the adsorbed adenoviral particles from said particles of adsorbent; and
        c. collecting the eluted adenoviral particles;
    wherein said particles of adsorbent comprise an agarose matrix and a central core comprising quartz, and dextran chains covalently coupled to said agarose matrix, on which are attached positively charged groups; and,
    ii) a gel filtration chromatography step that is carried out on a support comprising an alkyl dextran and methylene bisacrylamide matrix or an ethylene glycol and methacrylate matrix.

2. The method as claimed in claim 1, wherein said agarose matrix is a 6% cross-linked agarose matrix.

3. The method as claimed in claim 2, wherein said positively charged groups are Q groups.

4. The method as claimed in claim 1, wherein said particles of adsorbent are of heterologous sizes.

5. The method as claimed in claim 1, wherein said positively charged groups have the formula R—CH(OH)—CH$_2$—N$^+$—(CH$_3$)$_3$.

6. The method as claimed in claim 1, wherein said contacting step is carried out under pH conditions of between approximately 7.5 and approximately 9.5.

7. The method as claimed in claim 6, wherein said pH is approximately 8.5.

8. The method as claimed in claim 1, wherein said contacting step is carried out in a buffer equilibrated at a final NaCl concentration of 400 mM.

9. The method as claimed in claim 1, wherein said contacting step (c) is carried out under conductivity conditions of between approximately 25 and approximately 70 mS/cm.

10. The method as claimed in claim 9, wherein said conductivity conditions are between approximately 30 and approximately 40 mS/cm.

11. The method as claimed in claim 10, wherein said conductivity conditions are between approximately 30 and approximately 35 mS/cm.

12. The method as claimed in claim 1, wherein said eluting step is carried out by modifying the salinity or the pH used in the contacting step.

13. The method as claimed in claim 12, wherein said eluting step is carried out by increasing the salinity.

14. A protocol for producing adenoviral particles which can be used for gene therapy, comprising the following steps (i) and (ii);
   (i) producing a crude viral preparation, comprising:
      (a) infecting or transfecting a suitable cell line with at least one adenoviral vector of interest;
      (b) culturing said infected or transfected cell line under conditions which allow viral replication and the production of viral particles;
      (c) collecting the cells and/or the supernatant,
   (ii) purifying said adenoviral particles from crude viral preparation obtained at step (i)(c) according to the method of claim 1.

15. The protocol as claimed in claim 14, further comprising:
   (i) a cell rupture or lysis step after step (c), optionally followed by a step of degrading the nucleic acids, and/or
   (ii) a step for inactivating enveloped viruses.

16. The method as claimed in claim 1, wherein said gel filtration chromatography is carried out on a support comprising beads with a diameter of between 10 and 80 μm.

17. The protocol as claimed in claim 14, wherein said adenoviral vector is a recombinant adenoviral vector.

18. The protocol as claimed in claim 17, wherein said recombinant adenoviral vector is replication defective.

19. A protocol for producing adenoviral particles, comprising:
   (i) producing a crude viral preparation by a procedure comprising:
      (a) infecting or transfecting a suitable cell line with at least one recombinant adenoviral vector;
      (b) culturing said infected or transfected cell line under conditions which allow viral replication and the production of viral particles;
      (c) collecting the cells and/or the supernatant,
   (ii) lysing the cells and/or the supernatant collected at step (i)(c) by mechanical action,
   (iii) clarifying the lysate obtained at step (ii) by successive filtrations to remove the insoluble matter,
   (iv) degrading the nucleic acid in the clarified lysate obtained in step (iii) by the action of benzonase and concomitantly inactivating the enveloped viruses by the action of a mixture of tributylphosphate and polysorbate 80,
   (v) purifying said adenoviral particles from the viral preparation obtained at step (iv) according to the method of claim 1 further comprising concentrating the adenoviral particles collected in the fluidized bed chromatography step by diafiltration before submitting the concentrated adenoviral particles to the gel filtration chromatography step, and
   (vi) sterilizing the adenoviral particles collected at step (v).

* * * * *